United States Patent
Nave

(10) Patent No.: US 10,842,368 B2
(45) Date of Patent: Nov. 24, 2020

(54) SUCTION CATHETER WITH BRUSH AND METHOD OF USE FOR LENS CLEANING

(71) Applicant: ETVIEW Ltd., Misgav (IL)

(72) Inventor: Omri Nave, Misgav (IL)

(73) Assignee: AMBU A/S, Ballerup (DK)

( * ) Notice: Subject to any disclaimer, the term of this patent is extended or adjusted under 35 U.S.C. 154(b) by 464 days.

(21) Appl. No.: 15/618,376

(22) Filed: Jun. 9, 2017

(65) Prior Publication Data
US 2017/0367571 A1 Dec. 28, 2017

Related U.S. Application Data

(60) Provisional application No. 62/348,584, filed on Jun. 10, 2016.

(51) Int. Cl.
| | |
|---|---|
| *A61B 1/12* | (2006.01) |
| *A61M 16/04* | (2006.01) |
| *A61B 1/00* | (2006.01) |
| *A61B 1/015* | (2006.01) |

(Continued)

(52) U.S. Cl.
CPC .......... *A61B 1/126* (2013.01); *A61B 1/00091* (2013.01); *A61B 1/00094* (2013.01); *A61B 1/015* (2013.01); *A61B 1/06* (2013.01); *A61B 1/2676* (2013.01); *A61M 16/0463* (2013.01); *A61M 16/0486* (2014.02); *A61M 2209/10* (2013.01)

(58) Field of Classification Search
CPC . A61B 1/00091; A61B 1/00094; A61B 1/015; A61B 1/126; A61B 1/267; A61B 1/2676; A61B 1/00119; A61M 16/486; A61M 16/0463; A61M 2209/10
See application file for complete search history.

(56) References Cited

U.S. PATENT DOCUMENTS

| | | | | |
|---|---|---|---|---|
| 5,337,730 A | * | 8/1994 | Maguire | A61B 1/00091 600/157 |
| 5,363,838 A | | 11/1994 | George | |
| 5,400,771 A | | 3/1995 | Pirak | |

(Continued)

FOREIGN PATENT DOCUMENTS

| | | |
|---|---|---|
| CN | 201862108 U | 6/2011 |
| CN | 104660874 | 5/2015 |

(Continued)

OTHER PUBLICATIONS

Extended European Search Report issued by the European Patent Office, dated Nov. 7, 2017, for related European Patent Application No. 17175220.7; 7 pages.

*Primary Examiner* — Aaron B Fairchild
(74) *Attorney, Agent, or Firm* — Faegre Drinker Biddle & Reath LLP

(57) ABSTRACT

A method for cleaning the lens of a visualization device integrated into a ventilation tube positioned inside a patient, wherein the tube comprises a ventilation lumen and the lens is positioned proximal to the distal end of the ventilation lumen, the method comprising providing a suction catheter comprising a brush at its distal end; positioning the catheter inside the ventilation lumen such that the brush protrudes from the distal end of the ventilation lumen; and manipulating the catheter at its proximal end to cause the brush to make contact with the lens in order to clean the lens.

22 Claims, 12 Drawing Sheets

(51) Int. Cl.
*A61B 1/06* (2006.01)
*A61B 1/267* (2006.01)

(56) References Cited

U.S. PATENT DOCUMENTS

| | | | |
|---|---|---|---|
| 5,499,625 A | 3/1996 | Frass et al. | |
| 5,518,502 A * | 5/1996 | Kaplan | A61B 1/126 |
| | | | 600/156 |
| 5,535,759 A * | 7/1996 | Wilk | A61B 1/015 |
| | | | 128/898 |
| 5,630,795 A * | 5/1997 | Kuramoto | A61B 1/00068 |
| | | | 600/153 |
| 5,725,476 A | 3/1998 | Yasui et al. | |
| 5,735,792 A | 4/1998 | Vanden Hoek | |
| 5,775,322 A | 7/1998 | Silverstein et al. | |
| 5,803,898 A | 9/1998 | Bashour | |
| 5,904,648 A | 5/1999 | Arndt | |
| 5,941,816 A | 8/1999 | Barthel et al. | |
| 6,067,684 A * | 5/2000 | Kweon | A46B 7/04 |
| | | | 15/167.1 |
| 6,126,592 A | 10/2000 | Proch et al. | |
| 6,189,533 B1 | 2/2001 | Simon et al. | |
| 6,248,060 B1 | 6/2001 | Buess et al. | |
| 6,692,431 B2 | 2/2004 | Kazakevich | |
| 6,923,176 B2 | 8/2005 | Ranzinger | |
| 6,929,600 B2 | 8/2005 | Hill | |
| 7,013,899 B2 | 3/2006 | Alfery | |
| 7,052,456 B2 | 5/2006 | Simon | |
| 7,530,946 B2 | 5/2009 | Hartwick | |
| 7,938,119 B2 | 5/2011 | Chen | |
| 7,942,813 B2 | 5/2011 | Mackin | |
| 8,047,215 B1 | 11/2011 | Sasaki | |
| 8,226,571 B2 | 7/2012 | Landesberg | |
| 8,458,844 B2 | 6/2013 | Vazales | |
| 8,473,033 B2 | 6/2013 | Wood et al. | |
| 8,479,739 B2 | 7/2013 | Hirsh | |
| 8,534,287 B2 | 9/2013 | Vazales | |
| 8,584,678 B2 | 11/2013 | Pol | |
| 8,696,548 B2 | 4/2014 | Gilboa | |
| 8,696,685 B2 | 4/2014 | Gilboa | |
| 8,790,270 B2 | 7/2014 | Landesberg | |
| 8,863,746 B2 | 10/2014 | Totz | |
| 8,887,730 B2 | 11/2014 | Wood | |
| 8,932,207 B2 | 1/2015 | Greenburg | |
| 8,978,657 B2 | 3/2015 | Sandmore | |
| 8,998,798 B2 | 4/2015 | Hayman | |
| 9,055,881 B2 | 6/2015 | Gilboa | |
| 9,125,582 B2 | 9/2015 | Petersen | |
| 9,155,854 B2 | 10/2015 | Hayman | |
| 9,204,794 B2 | 12/2015 | Lisogurski et al. | |
| 9,211,060 B2 | 12/2015 | Waldron | |
| 9,242,058 B2 | 1/2016 | Hayman et al. | |
| 9,283,342 B1 | 3/2016 | Gardner | |
| 9,332,891 B2 | 5/2016 | Vazales | |
| 9,433,339 B2 | 9/2016 | Allyn | |
| 9,538,908 B2 | 1/2017 | Allyn | |
| 9,579,012 B2 | 2/2017 | Vazales | |
| 9,662,466 B2 | 5/2017 | Gunday | |
| 9,788,755 B2 | 10/2017 | Hayman | |
| 9,801,535 B2 | 10/2017 | Turnbull | |
| 9,855,111 B2 | 1/2018 | Vazales | |
| 9,907,624 B2 | 3/2018 | Vazales | |
| 10,149,602 B2 | 12/2018 | Daher et al. | |
| 10,478,054 B2 | 11/2019 | Nave et al. | |
| 2001/0028227 A1 | 10/2001 | Lys | |
| 2002/0045801 A1 | 4/2002 | Niida | |
| 2002/0062062 A1 | 5/2002 | Belson | |
| 2002/0076280 A1 | 6/2002 | Semotiuk | |
| 2002/0077527 A1 | 6/2002 | Aydelotte | |
| 2002/0108610 A1 | 8/2002 | Kent | |
| 2002/0193664 A1 | 12/2002 | Ross et al. | |
| 2003/0011538 A1 | 1/2003 | Lys | |
| 2003/0028078 A1 | 2/2003 | Glukhovsky | |
| 2003/0051733 A1 | 3/2003 | Kotmel et al. | |
| 2007/0137651 A1 | 6/2007 | Glassenberg et al. | |
| 2008/0188715 A1 | 8/2008 | Fujimoto | |
| 2008/0200764 A1 | 8/2008 | Okada | |
| 2009/0227998 A1 | 9/2009 | Aljuri | |
| 2009/0253964 A1 | 10/2009 | Shinichi | |
| 2010/0113916 A1 | 5/2010 | Kumar | |
| 2010/0249639 A1 | 9/2010 | Bhatt | |
| 2011/0151404 A1 | 6/2011 | Dombrowski | |
| 2011/0197888 A1 | 8/2011 | Deutsch | |
| 2012/0041534 A1 | 2/2012 | Clerc | |
| 2012/0172664 A1 | 7/2012 | Hayman | |
| 2012/0197086 A1 | 8/2012 | Morris et al. | |
| 2012/0259173 A1 | 10/2012 | Waldron et al. | |
| 2012/0302833 A1 | 11/2012 | Hayman | |
| 2013/0104884 A1 * | 5/2013 | Vazales | A61M 16/0418 |
| | | | 128/202.16 |
| 2013/0158351 A1 * | 6/2013 | Daher | A61M 16/04 |
| | | | 600/109 |
| 2013/0305469 A1 * | 11/2013 | Rodriguez Sanjuan | |
| | | | A61B 1/122 |
| | | | 15/104.05 |
| 2013/0324798 A1 | 12/2013 | Molnar et al. | |
| 2014/0039256 A1 | 2/2014 | Oren | |
| 2014/0046142 A1 | 2/2014 | Gavriely | |
| 2014/0150782 A1 * | 6/2014 | Vazales | A61M 16/0463 |
| | | | 128/202.16 |
| 2015/0099927 A1 | 4/2015 | Ali | |
| 2015/0174352 A1 | 6/2015 | Hayman | |
| 2015/0190044 A1 | 7/2015 | Livnat | |
| 2016/0183777 A1 | 6/2016 | Daher et al. | |
| 2016/0206189 A1 | 7/2016 | Nearman | |
| 2018/0296068 A1 | 10/2018 | Matthison-Hansen | |

FOREIGN PATENT DOCUMENTS

| | | |
|---|---|---|
| WO | WO 2013/063520 | 5/2013 |
| WO | WO 2014/134011 | 9/2014 |

* cited by examiner

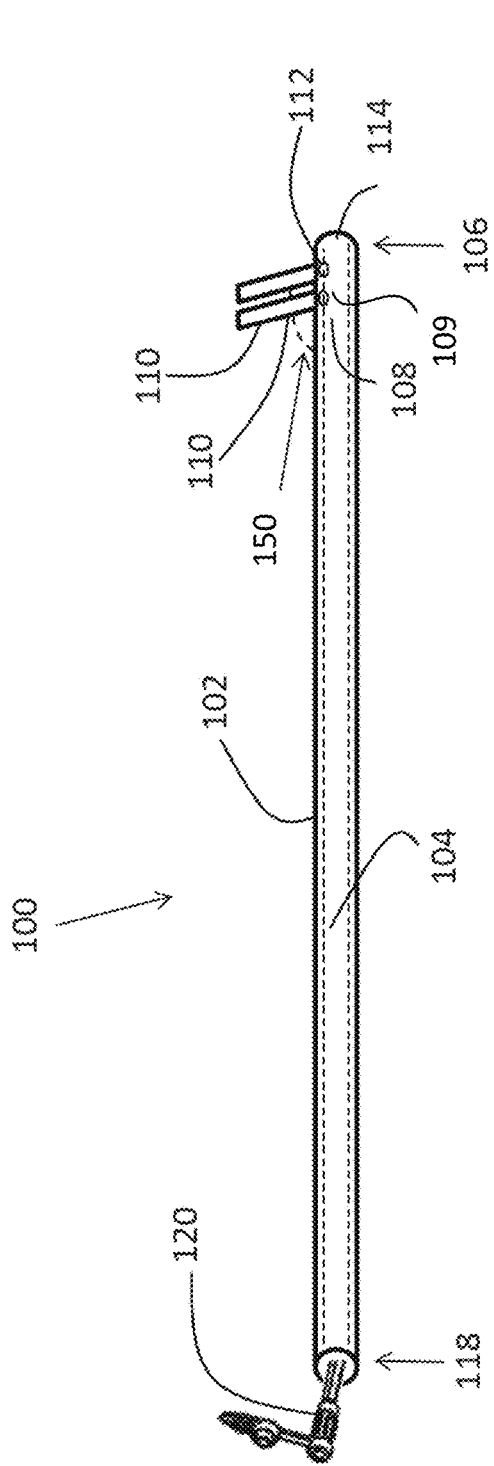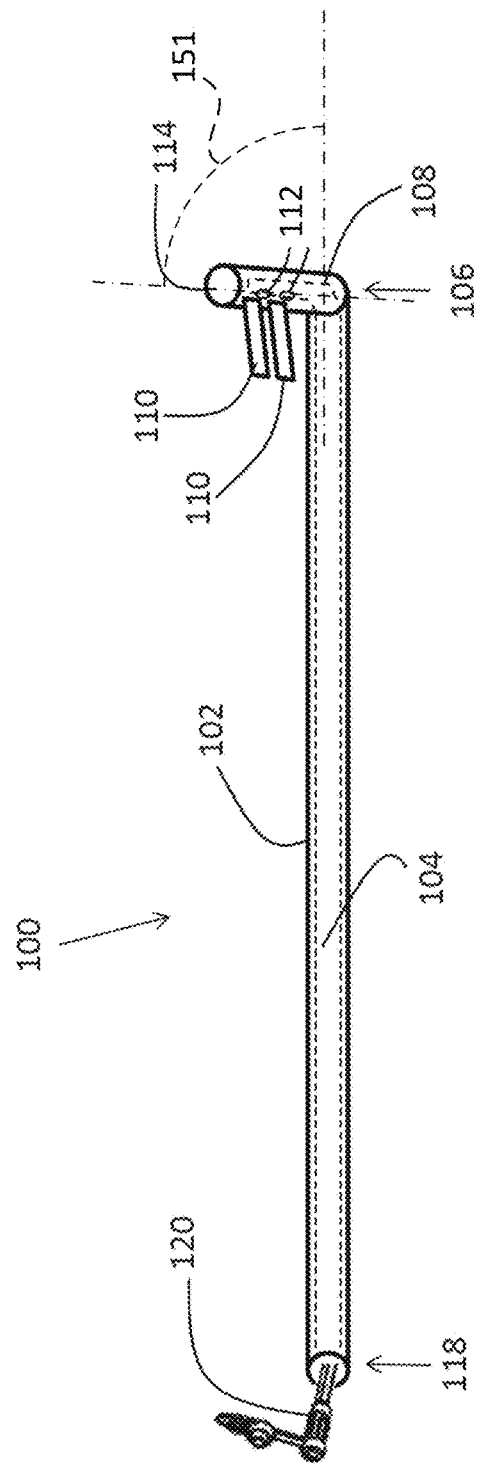

US 10,842,368 B2

SUCTION CATHETER WITH BRUSH AND METHOD OF USE FOR LENS CLEANING

CROSS-REFERENCE TO RELATED APPLICATIONS

This application claims the benefit of U.S. Patent Application No. 62/348,584, filed Jun. 10, 2016, which is incorporated by reference herein in its entirety.

FIELD OF THE INVENTION

The present invention relates to a suction catheter and, in particular, to a suction catheter with a brush adapted for cleaning a distal surface of a camera integrated in a tube inserted into a subject.

BACKGROUND OF THE INVENTION

An endotracheal tube may be inserted into the trachea of a patient who is in acute respiratory failure or is undergoing general anesthesia and requires artificial ventilation. Securing the tube and preventing its inadvertent movement during use is critical to the prevention of accidents. Inflating a cuff that surrounds the tube near its tip occludes the space between the outer wall of the tube and the inner wall of the trachea to provide an airtight seal and hold the tube in place. Once the tube has been inserted, it is mandatory to verify its correct position.

One method to verify the correct position of the tube requires a fiber optic bronchoscope. First the bronchoscope is connected to a light source to provide the needed illumination of the field facing its tip. The shaft of the bronchoscope is then inserted through the endotracheal tube and moved in as far as possible. The tip of bronchoscope is then inserted into the patient's airway and advanced, under visualization through the bronchoscope's eyepiece or a video display, in between the vocal folds into the trachea. The endotracheal tube can now be pushed down the bronchoscope's shaft and moved between the vocal folds into the trachea. The endotracheal tube can now be secured and the bronchoscope removed to free up the lumen of the endotracheal tube.

Another method to verify the correct position of the tube uses a ventilation tube with a built in camera such as that disclosed in U.S. patent application Ser. No. 13/737,944 hereby incorporated by reference as if fully set forth herein. The tube disclosed therein comprises cleaning nozzles for injection of fluid to clean a distal surface of the camera. However, accumulated debris, mucus or other dirt may not be sufficiently dislodged by the liquid or gas directed from the cleaning nozzles and physical wiping of the distal surface may be necessary. Removal of the tube for this purpose is preferably avoided.

There is an unmet need for, and it would be highly useful to have, a method and apparatus that allow cleaning/wiping of a distal surface of a camera of an endotracheal tube, endobronchial tube or other ventilation tube comprising a camera without the need to remove the tube from the patient.

SUMMARY OF THE INVENTION

The present invention overcomes the deficiencies identified above in the background by providing a suction catheter adapted for cleaning a distal surface of a camera that forms part of a ventilation tube. The suction catheter comprises a brush at its distal end. The brush is preferably angled to engage the distal surface of the camera. The catheter optionally comprises cleaning nozzles disposed proximal to or in between or within bristles of the brush.

A method is also provided for cleaning the distal surface of the camera of a ventilation tube already positioned in a patient.

According to a preferred embodiment of the present invention, there is provided a method for cleaning the distal surface of a visualization device integrated into a ventilation tube positioned inside a patient, wherein said tube comprises a ventilation lumen and said distal surface is positioned proximal to the distal end of said ventilation lumen, comprising:

a. providing a suction catheter comprising a brush at its distal end;
b. positioning said catheter inside said ventilation lumen such that said brush protrudes from the distal end of said ventilation lumen; and
c. manipulating said catheter to cause said brush to make contact with said distal surface in order to clean said distal surface of said camera.

Optionally said suction catheter comprises a catheter lumen and at least one cleaning nozzle disposed proximal to said brush and in fluid communication with said catheter lumen, further comprising injecting a liquid into said catheter lumen while said brush in proximal to said lens such that said liquid exits said at least one nozzle in the direction of said lens.

Optionally said brush comprises at least one bristle.

Optionally said at least one bristle has a cross-sectional shape selected from the group consisting of: circular, square, rectangular, hexagonal, and triangular.

According to at least some embodiments there is provided a suction catheter for cleaning a distal surface of a visualization device integrated into a ventilation tube positioned inside a patient, wherein said tube comprises a ventilation lumen and said distal surface is positioned proximal to the distal end of said ventilation lumen, said suction catheter comprising:

a. a hollow tube, and
b. a brush comprising at least one bristle disposed at the distal end of said tube.

Optionally said brush further comprises at least one cleaning nozzle.

According to at least some embodiments there is provided a ventilation tube comprising a ventilation lumen, a brush channel and a visualization device, said visualization device comprising a lens, wherein said lens is positioned proximal to the distal end of said ventilation lumen, said brush channel comprising an aperture and a brush extendable from said aperture, wherein said aperture is positioned proximal to said lens such that upon extending said brush from said aperture, said brush is able to contact said lens.

Optionally said brush channel further comprises a brush cable attached to said brush, wherein said brush cable is manipulated such that said brush is extended from said aperture.

Optionally the tube further comprises a light source positioned proximal to said lens, wherein said brush is able to contact said light source upon extending said brush from said aperture.

Optionally said ventilation lumen comprises a plurality of lumens for selective ventilation. Optionally said ventilation lumen comprises a single lumen.

Most preferably the catheter of the present invention may be made of medical grade materials for example including but not limited to plastic, rubber, polymers or silicone or the like materials as is known in the art.

Most preferably the ventilation tube provides for visualization during insertion and during continuous use of the oral cavity, esophagus, larynx trachea; the tracheal carina and at least a portion of a bronchus, optionally and more preferably portions of both bronchi.

Most preferably the integrated camera and light source provide continuous verification of the correct placement of the endotracheal tube. The continuous placement verification allows a caregiver the opportunity to detect any dangerous situation, for example cuff dislodgement, providing sufficient time to react to the situation as is necessary. Moreover blood and secretion accumulation or any other unexpected incidents during surgery, which might cause risk to the patient, may be observed.

Within the context of this application the term ventilation tube may be used interchangeably with any one of respiratory tube, endotracheal tube, endobronchial tube, single lumen tube, or double lumen tube, to collectively refer to a tube and/or catheter utilized for selectively ventilating a subject. The ventilation tube maintains airway patency and/or delivers anesthetic, inhalation agent or other medical gases, and secure ventilation.

A camera or visualization device includes an image sensor, one or more lenses in front of the sensor, and one or more illumination sources, such as light emitting diodes. The sensor, lenses and illumination source may be placed within a tube, preferably a cylindrical tube, with a transparent cover positioned at the distal end of the cylindrical tube to seal the components of the camera and protect them from moisture and debris. The term lens as used herein refers to the distal transparent cover of the visualization device or camera that is part of the ventilation tube. Thus the term lens may refer to the outer lens of the camera or to a flat transparent cover that protects this lens. The term lens may also refer to other exposed components of the visualization device such as lighting sources. As used herein, the distal surface of the camera or visualization device may be the distal, or exposed, surface of the lens or transparent cover.

Most preferably the image sensor may be associated with an auxiliary device for example including but not limited to a display and power supply at the proximal end of the tube most preferably about the first lumen, through a single dedicated connector for example including but not limited to a USB connector, a mini or micro USB connector, or a LEMO connector.

Optionally the ventilation tube may be adapted for non-invasive insertion through the oral cavity or nasal cavity. Optionally the ventilation tube may be adapted for insertion through an external port or incision. Optionally the ventilation tube may be adapted for insertion through a surgical procedure or other invasive procedure.

Unless otherwise defined, all technical and scientific terms used herein have the same meaning as commonly understood by one of ordinary skill in the art to which this invention belongs. The materials, methods, and examples provided herein are illustrative only and not intended to be limiting. The terms catheter and tube may be used interchangeably herein. The terms lumen and channel may be used interchangeably herein. The terms visualization device, image sensor, and camera are used interchangeably herein.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in order to provide what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 1A and 1B show illustrations of a suction catheter with a cleaning brush according to at least some embodiments of the present inventions;

DESCRIPTION OF THE PREFERRED EMBODIMENTS

The principles and operation of the present invention may be better understood with reference to the drawings and the accompanying description. The present invention, in at least some embodiments, is of a suction catheter adapted for cleaning an integrated camera of a ventilation tube when the tube is already positioned inside a patient.

Figure 2C:
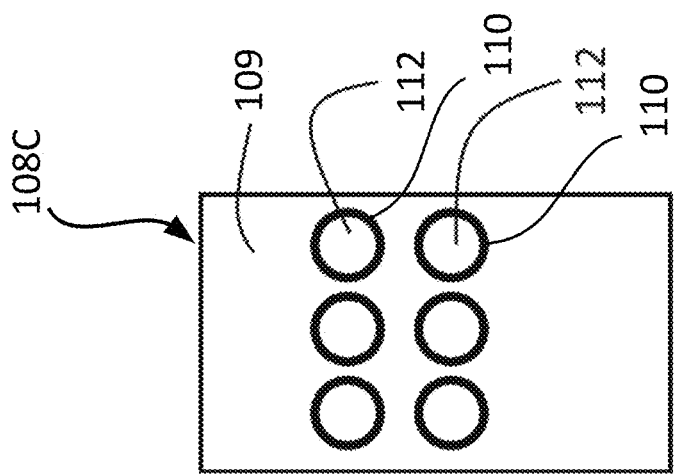
FIGS. 2A-2C are plan view illustrations of a catheter brush according to at least some embodiments of the present invention.
Figure 2B:
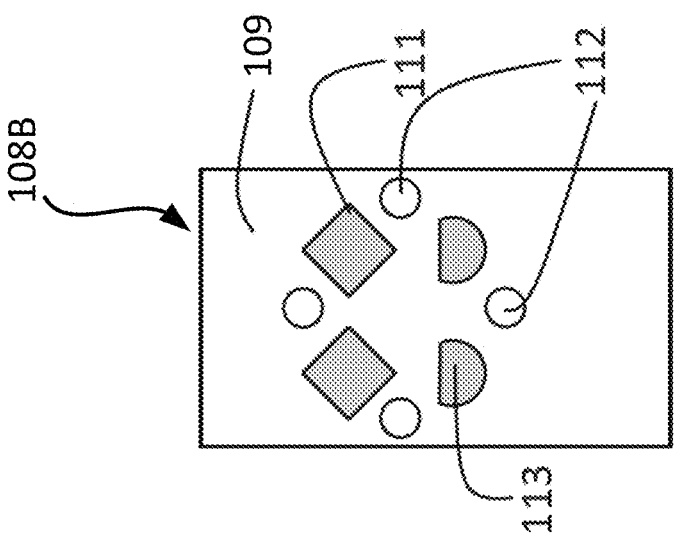
Figure 2A:
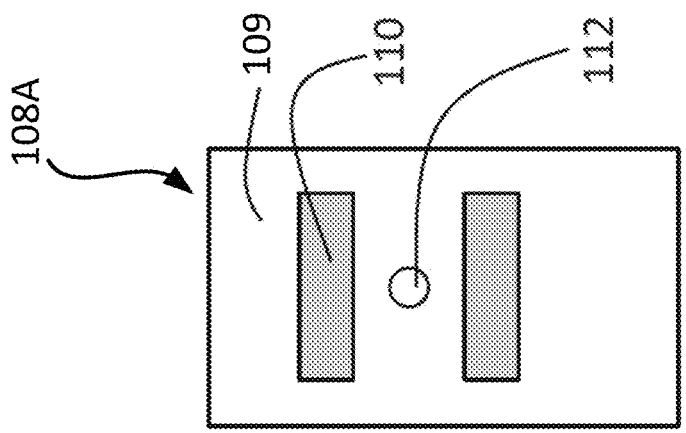

Reference is now made to FIGS. 1A and 1B which show an illustration of a suction catheter with a cleaning brush according to at least some embodiments of the present inventions. As shown in FIG. 1, suction catheter 100 comprises catheter tube 102. Catheter tube 102 is hollow, forming catheter lumen 104. Catheter tube 102 is adapted at its distal end 106 to form catheter brush 108. Brush 108 comprises bristles 110. In FIG. 1, two bristles 110 are shown for purposes of illustration. Brush 108 may comprise only one bristle 110 or any number of bristles as suited for the cleaning purpose of brush 108. Further embodiments of brush 108 are shown in FIGS. 2A-2C.

Bristles 110 have a cross-sectional shape that may be circular, rectangular, hexagonal, triangular, or any other suitable shape. Bristles 110 are formed of any biocompatible material suitable for cleaning the distal surface of the camera of the ventilation tube. The bristles may be substantially smooth or may comprise indentations, or projections to further enhance their cleaning capability. Bristles 110 preferably project from a base 109 of brush 108 at an angle 150. Angle 150 is preferably between 30 and 100 degrees. Bristles 110 may optionally be curved or bent. Bristles 110 preferably have the same dimensions. Alternatively, bristles 110 have different dimensions.

Brush 108 optionally comprises one or more cleaning nozzles 112. Nozzles 112 are in fluid communication with lumen 104. An injection port 120 on the proximal end 118 of suction catheter 100 enables injection of a liquid or gas for ejection via nozzles 112. Catheter 100 is preferably sealed at its distal tip 114 such that fluids injected via injection port 120 can only exit via nozzles 112. Alternatively injection port 120 may be connected to a suction device such that nozzles 112 will function as suction ports. Alternatively, distal tip 114 is open forming an aperture so as to be used for suction or for dispensing of fluids.

As shown in FIG. 1B, brush 108 is preferably angled with respect to catheter tube 102. The angle 151 of brush 108 is preferably between 15 and 90 degrees. Optionally, the connection point of brush 108 and catheter tube 102 is curved. Optionally the connection point is angled. Angles 150 and 151 are selected to ensure the ends of the bristles are able to clean the lens, as shown in FIGS. 3B and 3C. If angle 150 is 90 degrees and angle 151 is 90 degrees, for example, the bristles are parallel to catheter tube 102.

Reference is now made to FIGS. 2A-2C which are plan view illustrations of a catheter brush 108A-108C according to at least some embodiments of the present invention. As shown in FIG. 2A, brush 108A comprises two bristles 110 of rectangular cross section and one nozzle 112 disposed in between bristles 110. In FIG. 2B, brush 108B comprises two bristles 111 with rectangular cross sections, more specifically square cross sections, and two bristles 113 with approximately semicircular cross sections, more or less surrounded by four nozzles 112. In FIG. 2C, brush 108C comprises six bristles 110 with circular cross sections, wherein bristles 110 are hollow formed as nozzles at their respective distal ends. It should be appreciated that brush 108 may comprise any combination of these bristles, nozzles, bristle shapes, nozzle shapes and bristle and nozzle arrangements and the embodiments of FIGS. 2A-2C should not be considered limiting.

A brush 108 made from bristles 110, 111, 113 is typically formed of a hairlike structure, preferably from relative stiff hairs. As described below the bristles 110, 111, 113 in a brush 108 may have different shapes or geometry. This different geometry can comprise differences in the cross-sectional shape (e.g. as illustrated in FIGS. 2A-2C, a conical shape, a pyramidal shape, etc.) as well as differences in the length of each bristle 110, 111, 113. Also, different bristles 110, 111, 113 in the same brush 108 may be made from different materials having different characteristics, such as different rigidity or different surface properties.

Differences in surface properties as well as differences in overall shape of the different bristles 110 in a brush could be used for transporting e.g. slime or phlegm from the lens to some long bristles 110, 111, 113 of the brush 108 having a surface being slightly more hydrophilic than the lens surface. Further transport deeper into the brush 108 could be facilitated by the brush 108 comprising shorter bristles 110, 111, 113 being more hydrophilic than the long bristles 110, 111, 113.

The bristles may be formed as extruded protrusions together with base 109. After extrusion base 109 may be attached to catheter tube 102 of suction catheter 100 or to a cable 452 (reference FIGS. 4A and 4B) or cable 552 (reference FIG. 5A). As described above, the bristles may be bent when placed inside the brush channel of the ventilation tube or the ventilation lumen, and may comprise materials selected to enable the bristles to spring or return to their original shape once they exit the channel or lumen, which original shape comprises angle 150. The angle 151 of brush 108 is determined by the diameter of the channel or lumen, a smaller diameter limiting the angle 151.

Reference is now made to FIGS. 3A-3C and FIG. 3D which are respectively illustrations and a flowchart of the use of the suction catheter and brush for cleaning the distal surface of a camera integrated into a ventilation tube according to at least some embodiments of the present invention.

Figure 3A:
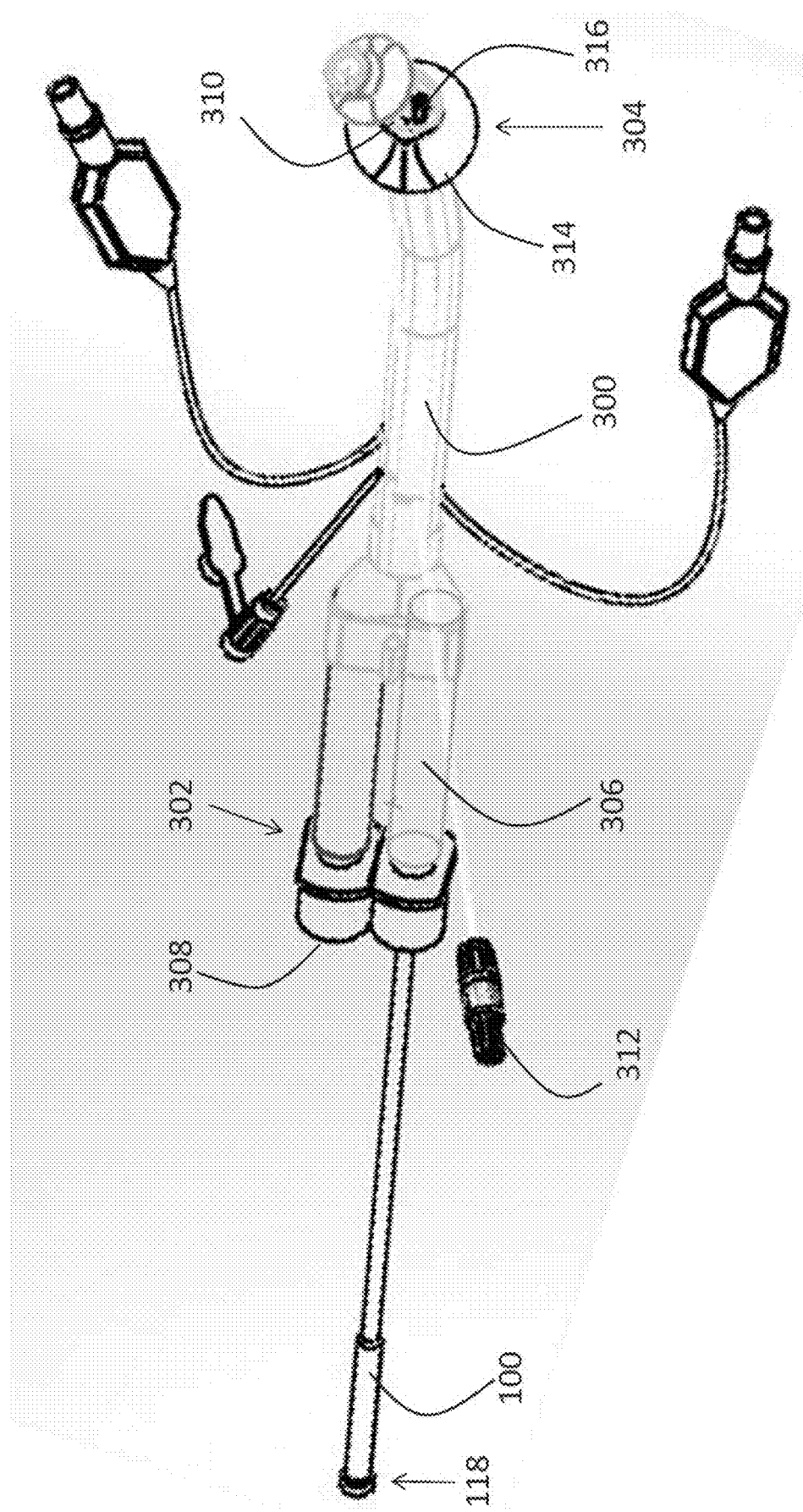
FIGS. 3A-3C are illustrations of the use of the suction catheter and brush for cleaning the lens of a camera integrated into a ventilation tube according to at least some embodiments of the present invention.
Figure 3B:
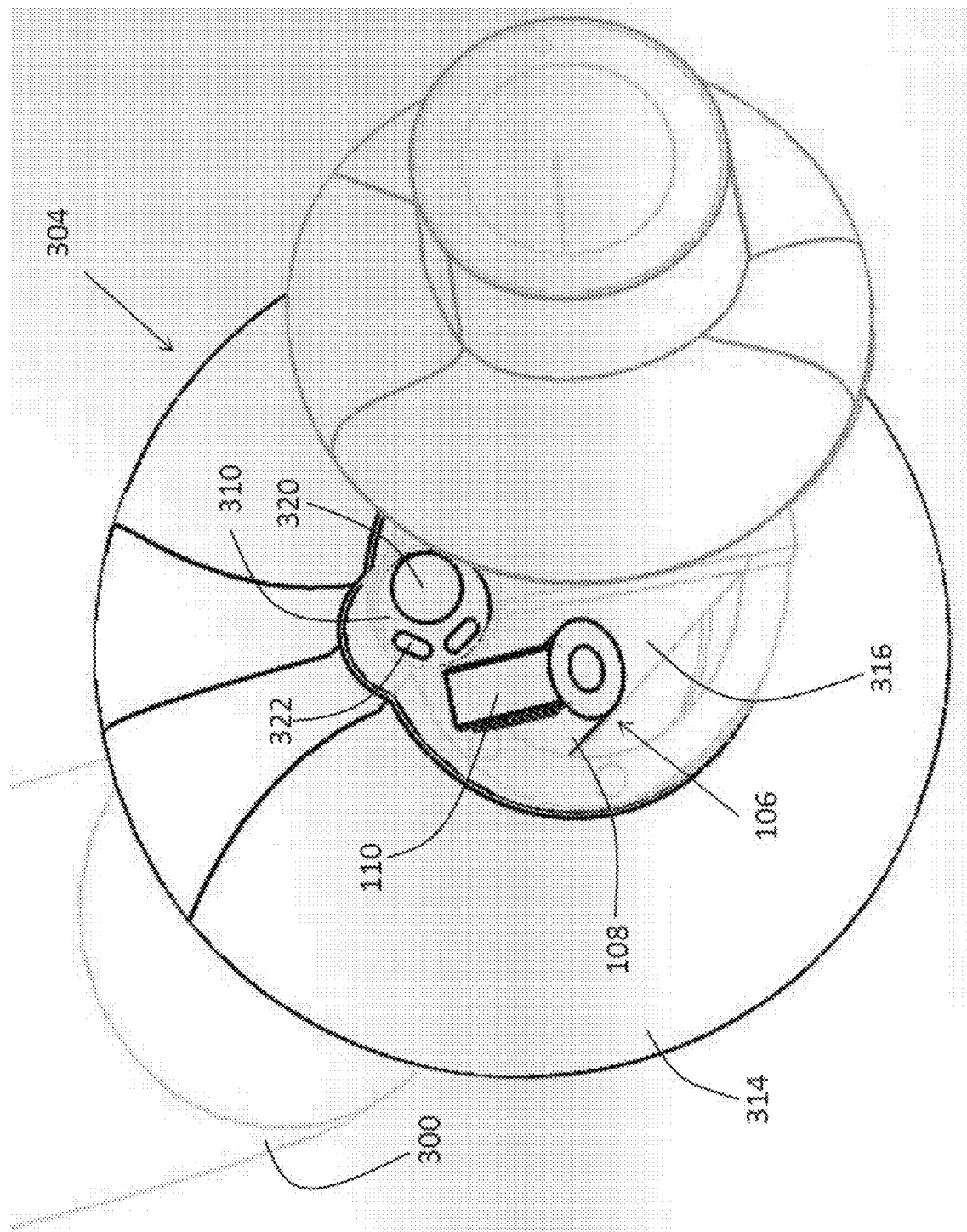
Figure 3C:
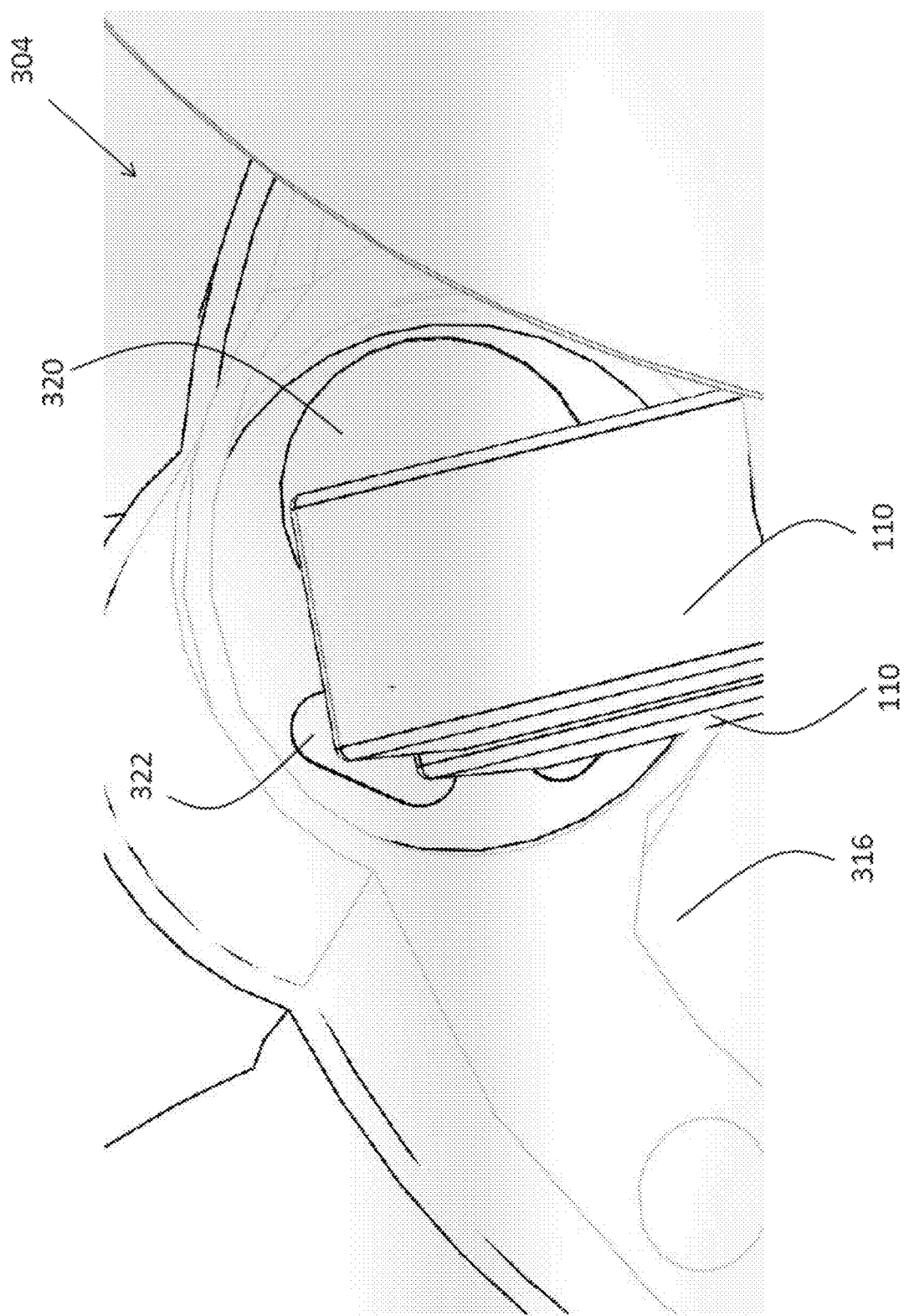

FIG. 3A shows an isometric view of an exemplary, non-limiting, illustrative ventilation tube 300. While FIG. 3A shows a dual lumen endobronchial tube, this should not be considered limiting as the tube 300 could be any ventilation tube with an integrated camera. As described herein, the terms "proximal" and "distal" are defined with regard to the point of entry to the subject, so that a proximal end 302 as shown remains outside the subject, while a distal end 304 as shown enters the subject (subject not shown in the figure).

At proximal end 302, a ventilator connector 306 connects tube 300 to a ventilator (not shown). Connector 306 features an aperture 308 for permitting two-way passage of fluids, including but not limited to gasses, into and out of the subject (not shown).

A visualization device 310 is located at the distal end 304 for visualizing at least a portion of the airways of the subject. Visualization device 310 is proximal to an aperture 316 of a ventilation lumen. Visualization device 310 may optionally comprise any suitable type of image sensor, including but not limited to a CCD image sensor or CMOS image sensor. Visualization device 310 is optionally in data communication with a visualization connector 312, to permit visual data to be transferred to an external device such as a video monitor (not shown).

A tracheal cuff 314 is located between proximal end 302 and distal end 304, but preferably closer to distal end 304. Tracheal cuff 314 is preferably deflated upon insertion of tube 300 to the subject and is then inflated once tube 300 is in place to maintain the position of tube 300 within the subject. Cuff 314 is here shown as inflated.

As shown in FIG. 3A, suction catheter 100, as described above with reference to FIGS. 1A and 1B, is inserted into tube 300 via connector 306. Optionally connector 306 is not present and then catheter 100 is inserted directly into tube 300. In the case of a double lumen tube, catheter 100 is inserted into the lumen with a distal end proximal to the camera.

FIG. 3B shows an enlarged view of the distal end 304 of the ventilation tube 300. FIG. 3B shows an enlarged view of visualization device 310 at distal end 304, for visualization of the subject when inserted to the subject. Visualization device comprises distal surface 320 as well as light source 322. Light source 322 may comprise one or more LEDs, optical fiber, waveguide, light guide, or any combination of these.

FIG. 3B also shows the distal end 106 of catheter 100 emerging from aperture 316 of a ventilation lumen of tube 300. Brush 108 and bristles 110 are also visible in FIG. 3B.

FIG. 3C shows a further enlarged view of the distal end 304 of the ventilation tube 300. As shown in FIG. 3C, bristles 110 make contact with light source 322 and distal surface 320 to clean these. Tube 300 optionally comprises cleaning nozzles (not shown) positioned proximal to visualization device 310.

Figure 3D:
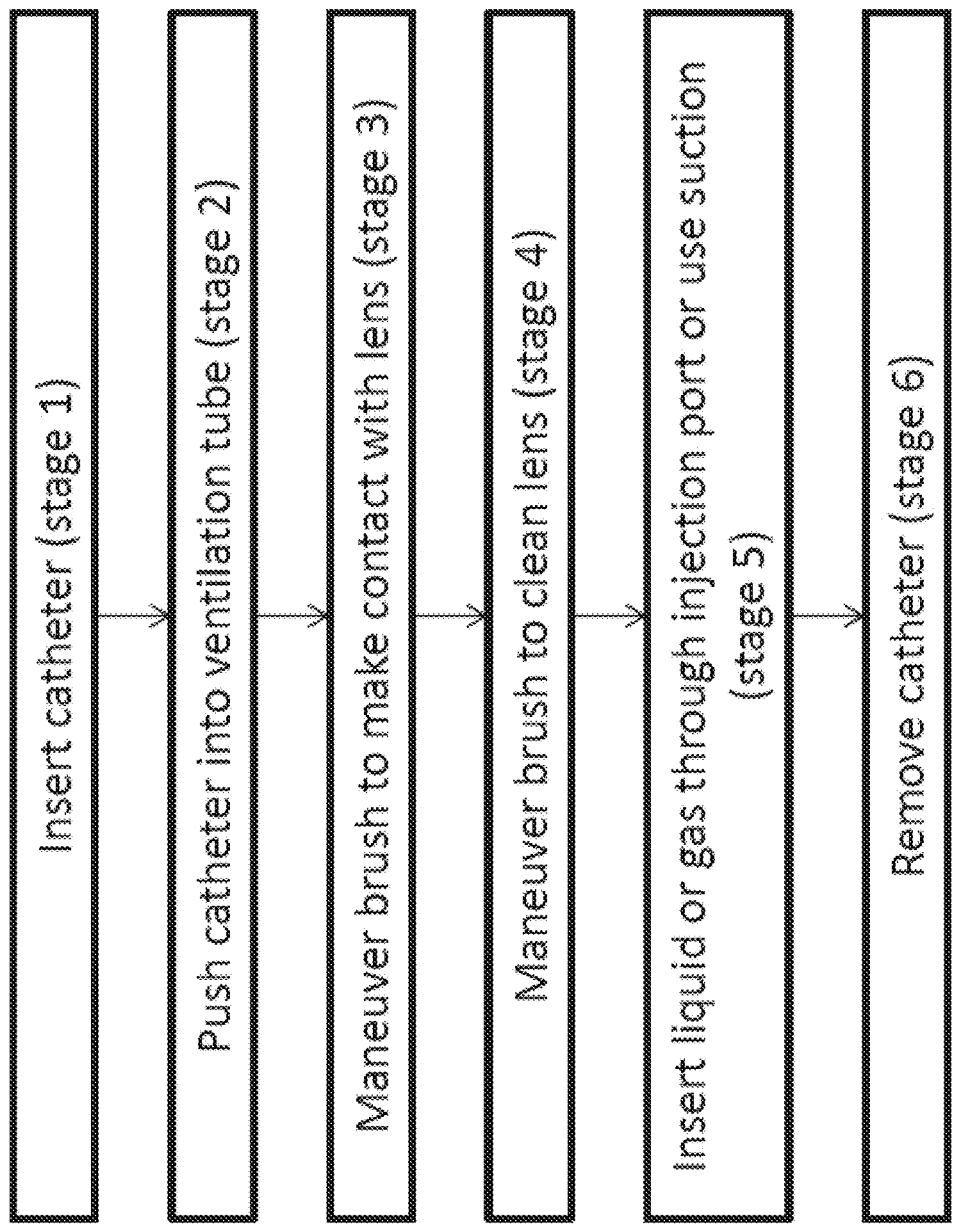
FIG. 3D is a flow diagram describing a preferred method for cleaning an integrated camera of a ventilation tube using the catheter described herein according to at least some embodiments of the present invention.

Reference is now made to FIG. 3D which is a flow diagram describing a preferred method for cleaning the distal surface of a camera integrated into a ventilation tube. In the described method of FIG. 3D, the ventilation tube 300 is first positioned in the patient and preferably secured in position by inflation of a cuff such as cuff 314. Visualization device 310 is connected to a display device and is activated to display the image and/or video captured by the visualization device 310.

In stage 1, the catheter 100 is inserted into the ventilation lumen of the ventilation tube 300. If the ventilation tube is already connected to a ventilation apparatus, then this will need to be disconnected before catheter 100 can be inserted. In stage 2, the catheter 100 is pushed into the ventilation lumen until the distal end 106 emerges from aperture 316 of the ventilation lumen. The emergence of distal end 106 can be verified via observation of the video feed from visualization device 310, such as on a display (not shown) connected to visualization device 310.

In stage 3, the brush 108 on distal end 106 is maneuvered to make contact with the distal surface 320 and/or light source 322. The distal end 106 is maneuvered by manipulating the proximal end 118 of catheter 100. The manipulation may include pushing, pulling, twisting and other movements performed by the practitioner. The contact with the visualization device 310 is verified as in stage 2 via observation of the video feed from visualization device 310. In stage 4 the catheter 100 is further manipulated as in stage 3 in order that bristles 110 clean distal surface 320 and/or light source 322 by wiping, brushing or other physical contact that dislodges debris, secretions or other material that is blocking distal surface 320 and/or light source 322. Optionally or additionally, in stage 4, cleaning of the distal surface is performed via suction through nozzles 112 or through open distal tip 114.

Optionally, in stage 5, a fluid such as a liquid or gas can be injected into catheter 100 through injection port 120 to exit via nozzles 112 to further assist with cleaning of distal surface 320 and/or light source 322. Optionally suction may be applied to injection port such that material wiped or brushed from visualization device 310 by bristles 110, 111, 113 may be removed. Suctioning may be via nozzles 112 or via catheter aperture at distal tip 114. Optionally, the activities of stage 5 are supplemented via fluid sprayed from the nozzles (not shown) of ventilation tube 300.

When the visualization device 310 is sufficiently clean the catheter 100 can be removed as at stage 6. Catheter 100 is withdrawn from the ventilation lumen which may then be reconnected or connected to a ventilation device as required.

Figure 4A:
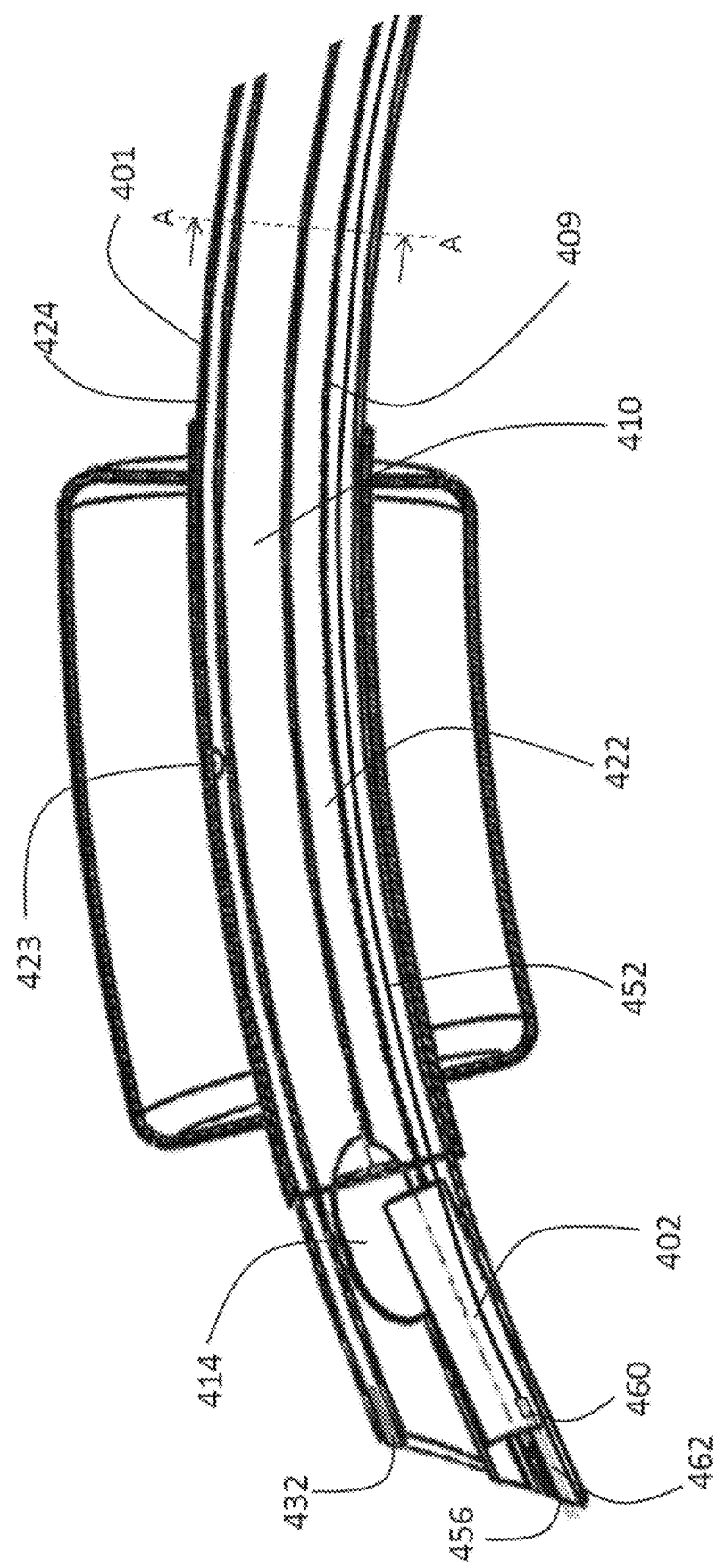
FIGS. 4A-4D show a single lumen ventilation tube with an integrated lens cleaning brush according to at least some embodiments of the present invention.

Reference is now made to FIGS. 4A-4D which show a ventilation tube with an integrated camera cleaning brush according to at least some embodiments of the present invention. FIG. 4A shows a complete cut-away view of an exemplary, non-limiting, illustrative single lumen endotracheal tube according to at least some embodiments of the present invention. While a single lumen endotracheal tube is shown, it should be appreciated that the integrated brush as described below could be integrated into any ventilation tube with an integrated camera and the descriptions of a single lumen tube should be considered non-limiting.

The cutaway is shown at the location of tracheal cuff 404 (tracheal cuff 404 is also shown cut-away). As shown, ventilation tube 401 comprises an external wall 430 with a plurality of internal channels or lumens. Ventilation lumen or tube 410 is provided for conveying gasses into and out of the subject; as such ventilation lumen 410 is typically the largest lumen within tube 401. Ventilation lumen has a distal end at aperture 417.

A visualization channel 422 embedded in the wall 430 of tube 401 preferably provides a path for cable 409 for connecting the visualization device 402 to a visualization connector (not shown). Visualization channel 422 has a distal end that houses visualization device 402. Visualization device 402 comprises distal surface 421 and light source 426.

Tracheal cuff 404 is fixedly attached to the external surface of tube 401. Tracheal cuff 404 is inflated through tracheal cuff inflator port 423 which opens into the inner volume of cuff 404 as shown. Tracheal cuff inflator port 423 receives air from enclosed tracheal cuff inflator channel 424 which is embedded in the wall 430 of tube 401 and which is in fluid communication at its proximal end with an inflation tube (not shown), which in turn receives air through an inflation connector (not shown). Tracheal cuff inflator channel 424 is sealed at its distal end by seal 432.

A brush channel 450 embedded in the wall 430 of tube 401 provides a path for brush cable 452 for connecting to a brush 460. Brush cable 460 extends at its proximal end out of ventilation tube 401 to allow manipulation for maneuvering brush 460. Cable 452 is suitably rigid to allow manipulation at its proximal end to be transferred to its distal end thus resulting in maneuvering of brush 460. Manipulation may include pushing, pulling, twisting and other required movements. Pushing brush cable 452 forward moves brush 460 out of aperture 456 of bristle channel 450. Brush 460 comprises bristles 462 that are bent so as to make contact with distal surface 421 and light source 426 when extended. Bristles 462 may comprise any of the bristles 110, 111, 113 and variations thereof. A limited number of bristles are shown for purposes of illustration and it should be appreciated that brush 460 may comprise only one or as many bristles as necessary for the purposes of cleaning distal surface 421 and light source 426.

Bristles 462 are sufficiently rigid so as to dislodge debris or any obstruction that has accumulated on the surface of distal surface 421 or light source 426. As with the embodiment described above with reference to FIGS. 3A-3D, the image captured by visualization device 402 may be used to guide the manipulation of brush 460 to clean distal surface 421 and/or light source 426.

Figure 4B:
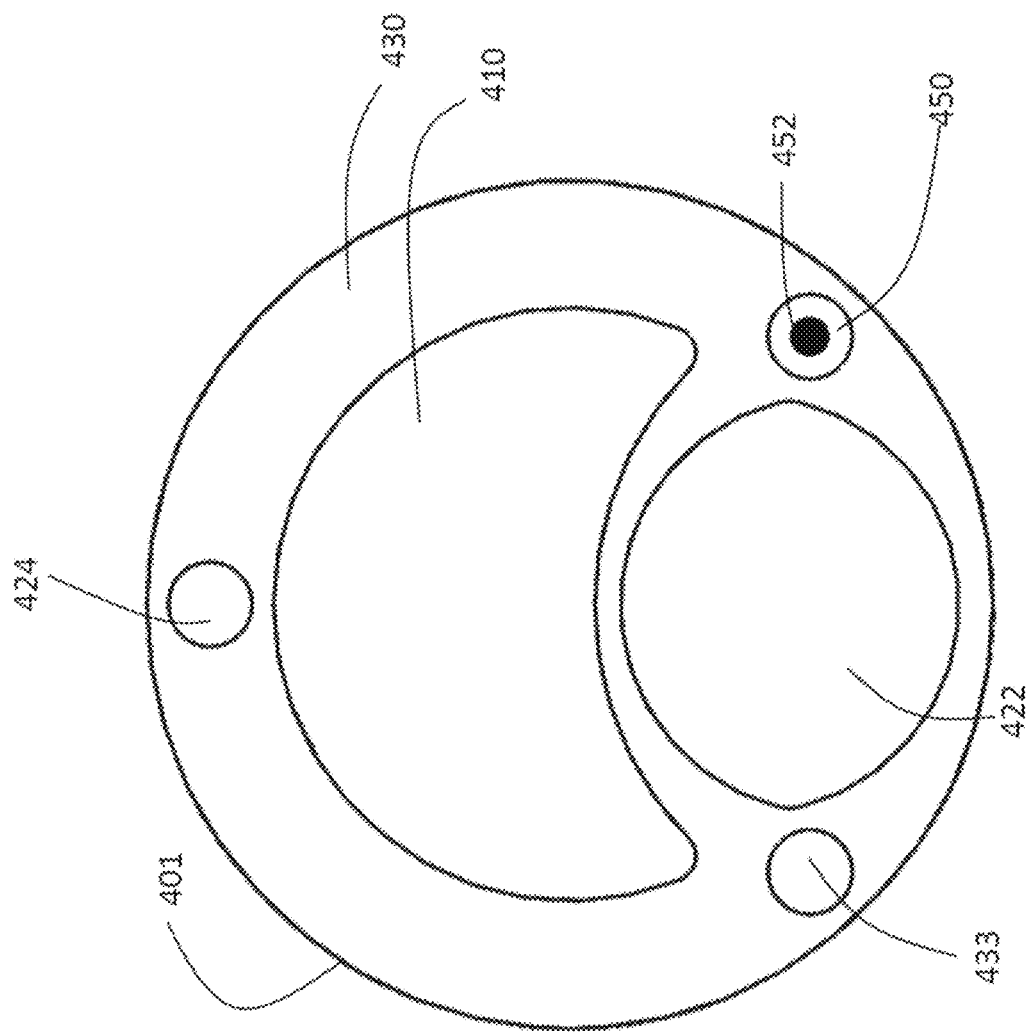

FIG. 4B shows a cross-section of the ventilation tube 401 of FIG. 4A. FIG. 4B shows channels embedded in the external wall 430 of tube 401. FIG. 4B is cross section A-A as shown in FIG. 4A. The channels embedded in wall 430 comprise: inflation channel 424 for inflating tracheal cuff 404, injection channels 433 that feed nozzles 407, brush channel 450, and visualization channel 422. Brush channel 450 provides a path for brush cable 452. The inner space within tube 401 defines ventilation lumen 410.

Figure 4C:
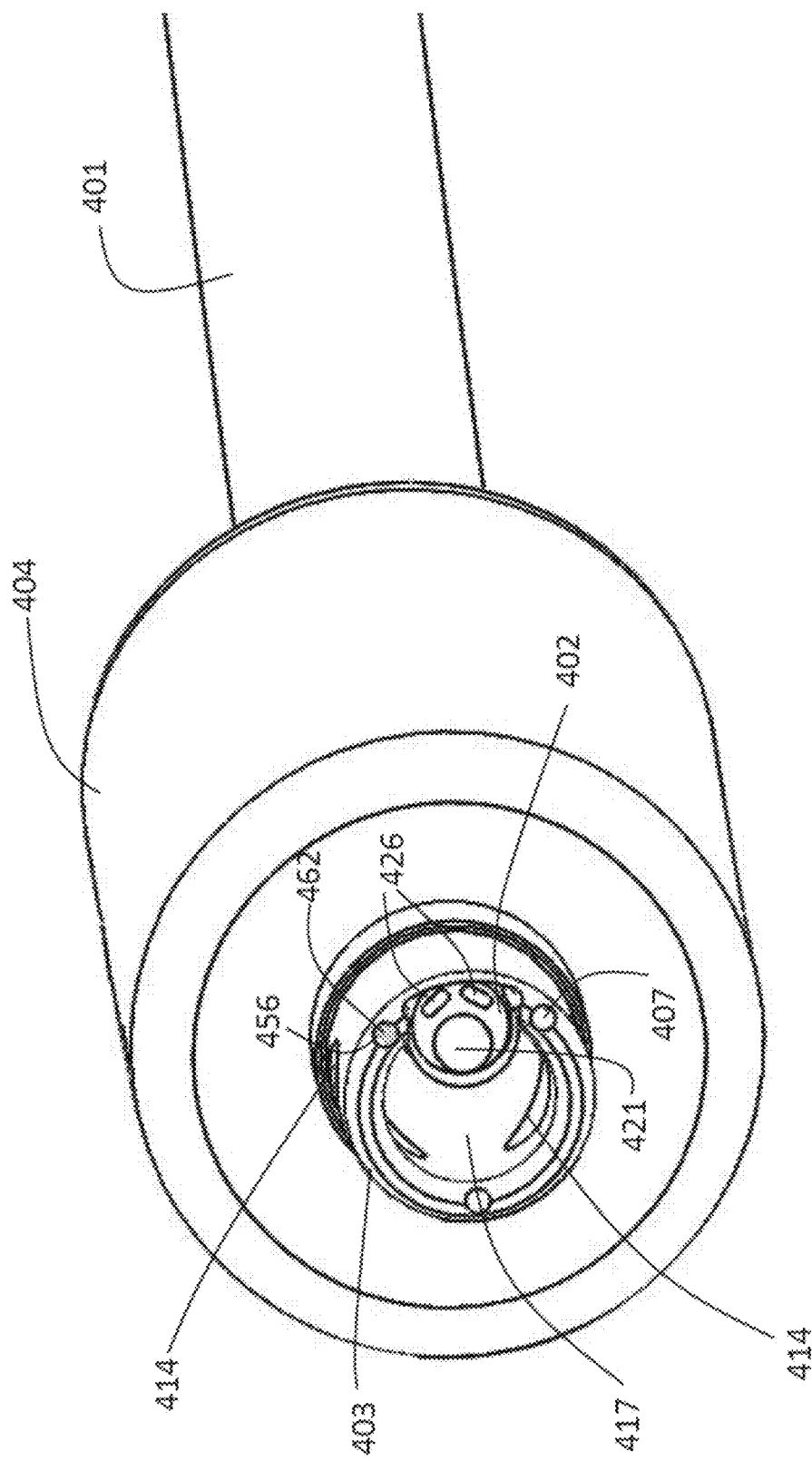

FIG. 4C shows an enlarged view of the tip of the ventilation tube 401. After insertion, visualization device 402 is used to confirm that tube 401 remains correctly positioned within the subject by visualizing the field (area) surrounding tip 403. Visualization device comprises distal surface 421 covering the image sensor as well as light source 426. Light source 426 may comprise one or more LEDs, optical fiber, waveguide, light guide, or any combination of these.

Nozzle 407 by its location and optionally also angle is aimed to direct a stream of fluid, such as a liquid for example, toward or at visualization device 402 in order to clean distal surface 421 or light source 426. As shown in FIG. 4C bristles 462 extend out of aperture 456.

Figure 4D:
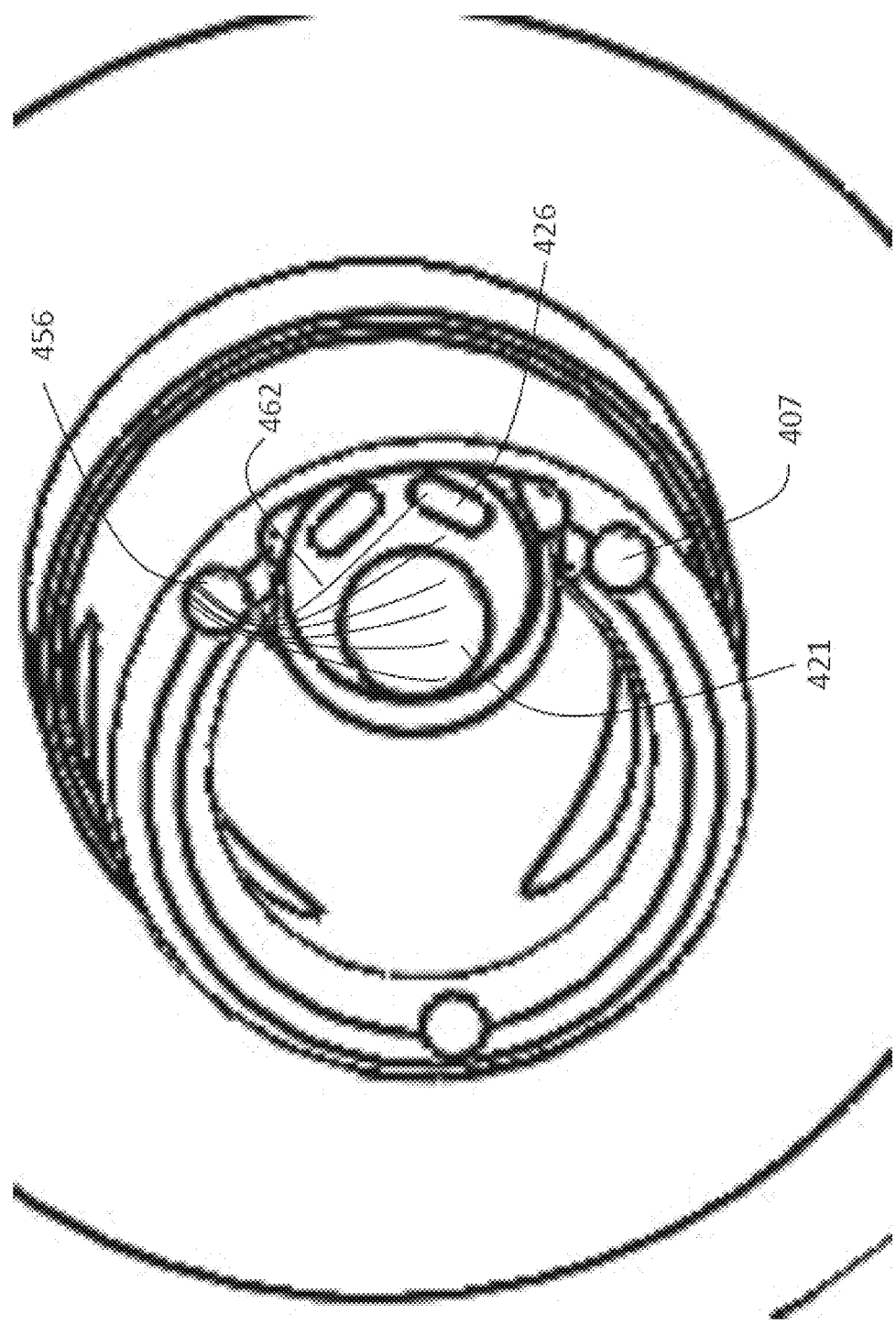

FIG. 4D shows a further enlargement of the tip of the ventilation tube 401. In FIG. 4D, brush 460 is shown as extended out of brush channel 450 via aperture 456. As shown, bristles 462 are bent or angled such that they make contact with distal surface 421 and light source 426 when extended. As described above, bristles 462 are maneuvered in order to clean distal surface 421 and/or light source 426.

Figure 5A:
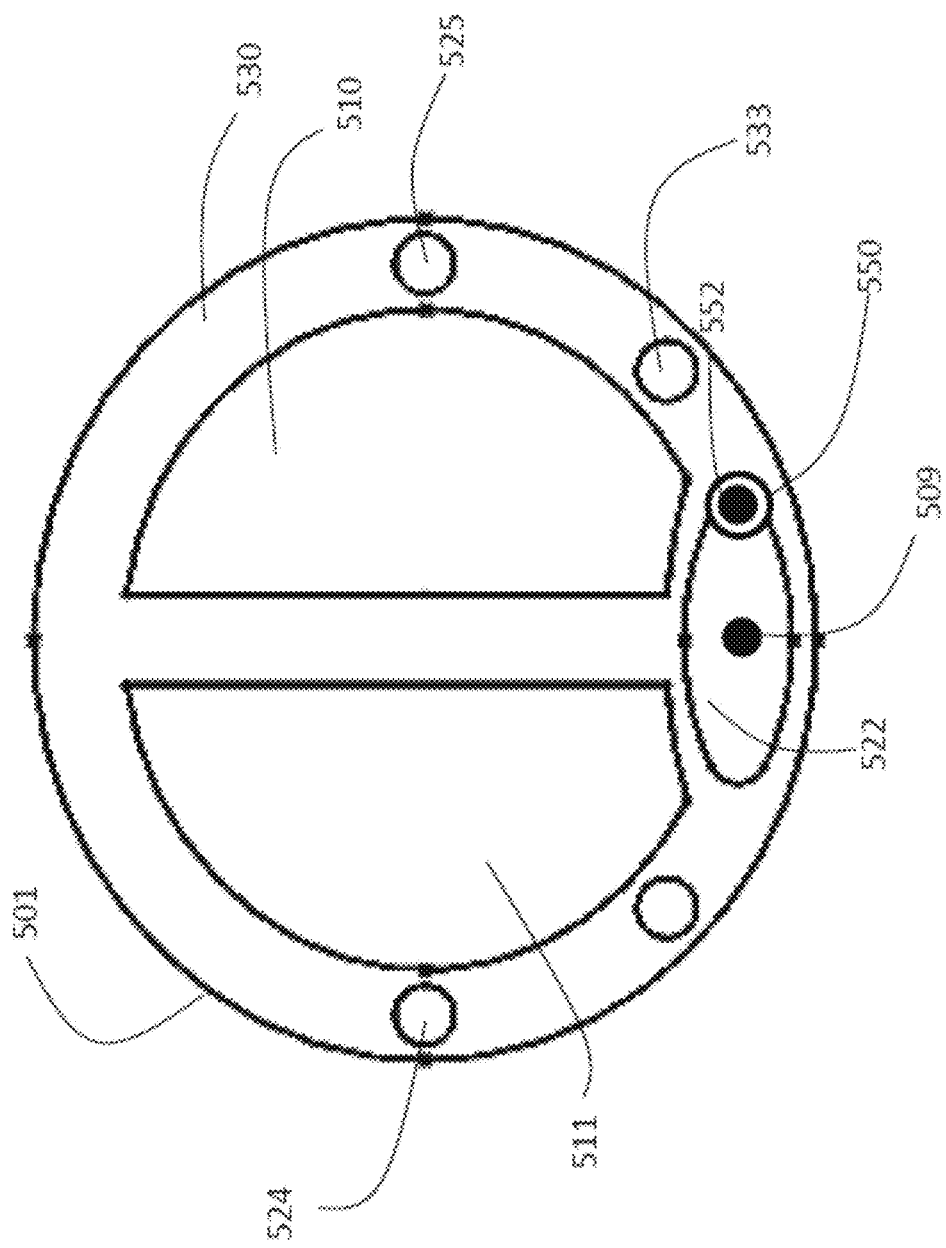
FIGS. 5A and 5B show a double lumen ventilation tube with an integrated lens cleaning brush according to at least some embodiments of the present invention.
Figure 5B:
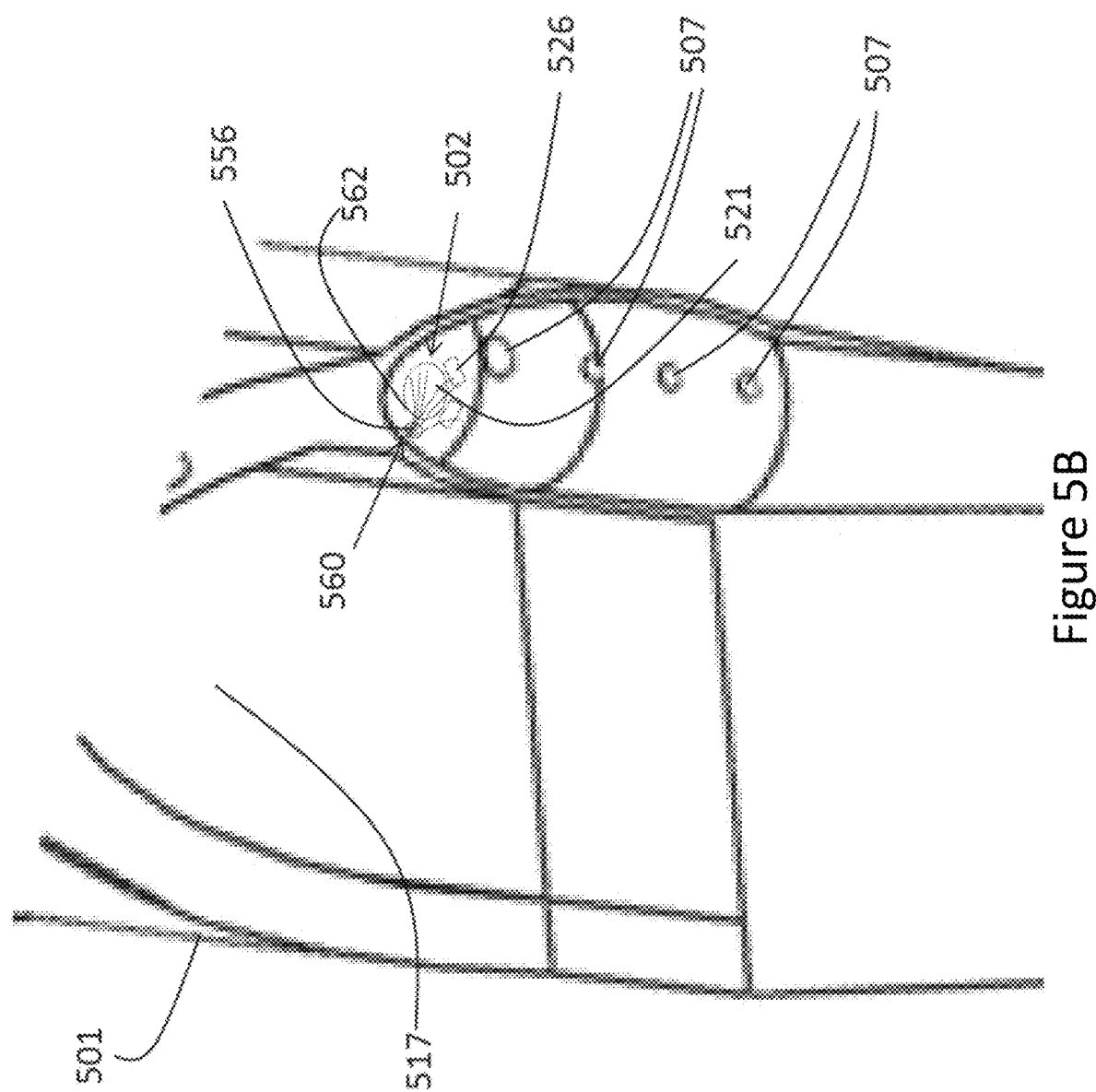

Reference is now made to FIGS. 5A-5B which show a dual lumen ventilation tube with an integrated distal surface cleaning brush according to at least some embodiments of the present invention. While a dual lumen endobronchial tube is shown, it should be appreciated that the integrated brush as described below could be integrated into any ventilation tube with an integrated camera and the descriptions of a dual lumen tube should be considered non-limiting.

FIG. 5A shows a cross-section of ventilation tube 501 and FIG. 5B shows an enlarged view of the aperture 517 of the tracheal lumen of ventilation tube 501. As shown, ventilation tube 501 comprises an external wall 530 with a plurality of internal channels or lumens. The channels embedded in wall 530 comprise: inflation channels 524 and 525 for inflating a tracheal cuff (not shown) and a bronchial cuff (not shown), injection channel 533 that feeds nozzles 507, brush channel 550, and visualization channel 522. Visualization channel 522 embedded in the wall 530 of tube 501 preferably provides a path for a visualization cable 509 for connecting the visualization device 502 to a visualization connector (not shown). Visualization channel 522 has a distal end that houses visualization device 502.

Visualization device 502 comprises distal surface 521 and light source 526. The dual inner spaces within tube 501 define dual ventilation lumens 510 and 511 for ventilation of the trachea and bronchus according to usage of an endobronchial tube.

Brush channel 550 provides a path for brush cable 552 for connecting to a brush 560. Brush cable 560 extends at its proximal end out of tracheal ventilation tube 501 to allow manipulation for maneuvering brush 560. Cable 552 is suitably rigid to allow manipulation at its proximal end to be transferred to its distal end thus resulting in maneuvering of brush 560. Manipulation may include pushing, pulling, twisting and other required movements. Pushing brush cable 552 forward moves brush out of aperture 556. Brush 560 comprises bristles 562 that are bent so as to make contact with distal surface 521 and light source 526 when extended. A limited number of bristles are shown for purposes of illustration and it should be appreciated that brush 560 may comprise only one or as many bristles as necessary for the purposes of cleaning distal surface 521 and light source 526.

Bristles 562 are sufficiently rigid so as to dislodge debris or any obstruction that has accumulated on the surface of distal surface 521 or light source 526. As with the embodiment described above with reference to FIGS. 3A-3D, the image captured by visualization device 502 may be used to guide the manipulation of brush 560 to clean distal surface 521 and/or light source 526.

After insertion into a patient, visualization device 502 is used to confirm that tube 501 remains correctly positioned within the subject by visualizing the field (area) surrounding aperture 517. Visualization device comprises distal surface 521 covering the image sensor as well as light source 526. Light source 526 may comprise one or more LEDs, optical fiber, waveguide, light guide, or any combination of these.

Nozzles 507 by their location and optionally also angle are aimed to direct a stream of fluid, such as a liquid for example, toward or at visualization device 502 in order to clean distal surface 521 or light source 526. In FIG. 5B, brush 560 is shown as extended out of brush channel 550 via aperture 556. As shown, bristles 562 are bent or angled such that they make contact with distal surface 521 and light source 526 when extended. As described above, bristles 562 are maneuvered in order to clean distal surface 521 and/or light source 526.

While the invention has been described with respect to a limited number of embodiments, it will be appreciated that many variations, modifications and other applications of the invention may be made.

What is claimed is:

1. A method for cleaning a distal surface of a visualization device, the method comprising:
   providing a ventilation tube including a ventilation lumen and the visualization device, the visualization device comprising a distal surface positioned proximal of an aperture at a distal end of the ventilation lumen;
   providing a suction catheter comprising a distal tip, a catheter lumen, and a brush at the distal tip, wherein the brush is sized and configured to contact the distal surface;
   positioning the suction catheter inside the ventilation lumen such that the brush protrudes from the distal end of the ventilation lumen; and
   manipulating the suction catheter to cause the brush to make contact with and thereby clean the distal surface of the visualization device.

2. The method of claim 1, wherein the distal surface is positioned proximal to the distal end of the ventilation lumen.

3. The method of claim 1, wherein the suction catheter comprises at least one cleaning nozzle disposed proximal to the brush and in fluid communication with the catheter lumen, the method further comprising injecting a liquid into the catheter lumen while the brush in proximal to the distal surface such that the liquid exits the at least one nozzle in the direction of the distal surface.

4. The method of claim 1, wherein the brush comprises at least one bristle.

5. The method of claim 4, wherein the at least one bristle has a cross-sectional shape selected from the group consisting of: cylindrical, rectangular, hexagonal, and triangular.

6. The method of claim 1, wherein the brush comprises at least two bristles being distinct from each other on at least one parameter selected from: shape, material, and surface properties.

7. The method of claim 1, wherein the brush comprises hollow bristles fluidly coupled to the catheter lumen, and wherein the suction catheter is capable of discharging a fluid injected at a proximal end of the catheter lumen through the hollow bristles to clean the distal surface of the visualization device.

8. The method of claim 1, wherein positioning the suction catheter inside the lumen includes:
   bending bristles of the brush while inserting the brush into a proximal end of the ventilation lumen until the bristles fit inside the ventilation lumen; and
   translating the suction catheter through the ventilation lumen until the brush extends distally of the distal end of the ventilation lumen sufficiently to enable the bent bristles to regain their unbent shape.

9. A ventilation system comprising:
   a ventilation tube including a ventilation lumen and a visualization device comprising a distal surface positioned proximal of an aperture at a distal end of the ventilation lumen; and
   a suction catheter including a distal tip, a catheter lumen, and a brush at the distal tip of the suction catheter, wherein the brush is sized and configured to contact the distal surface.

10. The ventilation system of claim 9, the suction catheter comprising:

a hollow tube defining the catheter lumen, wherein the brush comprises at least one bristle.

11. The ventilation system of claim 10, wherein the visualization device is positioned proximal to the distal end of the ventilation lumen.

12. The ventilation system of claim 10, wherein the brush further comprises at least one cleaning nozzle.

13. The ventilation system of claim 10, wherein the brush comprises hollow bristles fluidly coupled to the hollow tube, including the at least one bristle, and the hollow bristles being capable of discharging a fluid supplied through the hollow tube toward the visualization device.

14. The ventilation system of claim 9, the ventilation tube further comprising a light source, wherein the brush is operable to contact the light source.

15. The ventilation system of claim 9, wherein the ventilation lumen comprises a plurality of lumens for selective ventilation.

16. The ventilation system of claim 9, wherein the ventilation lumen comprises a single ventilation lumen.

17. The ventilation system of claim 9, wherein the brush comprises bristles and at least one cleaning nozzle.

18. The ventilation system of claim 17, wherein the brush comprises a base and the bristles extend from the base at an angle between 30 and 100 degrees.

19. The ventilation system of claim 17, wherein the at least one cleaning nozzle is fluidly coupled with the catheter lumen.

20. The ventilation system of claim 19, wherein the distal tip is sealed and the at least one cleaning nozzle is operable to suction fluids through the catheter lumen.

21. The ventilation system of claim 17, wherein the at least one cleaning nozzle is disposed proximal to the brush and in fluid communication with the catheter lumen, whereby injection of a liquid into the catheter lumen causes the liquid to exit the at least one nozzle in the direction of the distal surface.

22. The ventilation system of claim 10, wherein the brush comprises a base that extends from a longitudinal axis of the hollow tube at an angle between 15 and 90 degrees.

* * * * *